United States Patent
Min et al.

(10) Patent No.: US 10,300,004 B2
(45) Date of Patent: May 28, 2019

(54) COSMETIC COMPOSITION FOR PREVENTING OR AMELIORATING SKIN DAMAGE CAUSED BY ULTRAVIOLET LIGHT

(71) Applicant: CUSKIN CO., LTD, Seoul (KR)

(72) Inventors: Hyung-Geun Min, Seoul (KR); Won-Serk Kim, Seoul (KR); Choon-Young Choi, Chuncheon-si (KR); Wang-Kyun Kim, Ansan-si (KR); Jin-Ho Lee, Incheon (KR)

(73) Assignee: CUSKIN CO., LTD., Seoul (KR)

( * ) Notice: Subject to any disclaimer, the term of this patent is extended or adjusted under 35 U.S.C. 154(b) by 0 days.

(21) Appl. No.: 15/754,851

(22) PCT Filed: Aug. 23, 2016

(86) PCT No.: PCT/KR2016/009283
§ 371 (c)(1),
(2) Date: Feb. 23, 2018

(87) PCT Pub. No.: WO2017/034288
PCT Pub. Date: Mar. 2, 2017

(65) Prior Publication Data
US 2018/0235863 A1    Aug. 23, 2018

(30) Foreign Application Priority Data

Aug. 25, 2015   (KR) .................. 10-2015-0119590

(51) Int. Cl.
*A61Q 17/04*    (2006.01)
*A61K 8/55*    (2006.01)
*A61Q 19/00*    (2006.01)

(52) U.S. Cl.
CPC ............... *A61K 8/55* (2013.01); *A61Q 17/04* (2013.01); *A61Q 19/004* (2013.01)

(58) Field of Classification Search
None
See application file for complete search history.

(56) References Cited

U.S. PATENT DOCUMENTS

2007/0225255 A1    9/2007    Frohlich et al.
2009/0258841 A1    10/2009    Murphy et al.

FOREIGN PATENT DOCUMENTS

| EP | 1 074 244 A2 | 2/2001 |
|---|---|---|
| JP | 2004-196759 A | 7/2004 |
| KR | 10-2012-0041965 A | 5/2012 |

OTHER PUBLICATIONS

Dong et al., "Mitochondrial Targeting of Vitamin E Succinate Enhances Its Pro-apoptotic and Anti-cancer Activity via Mitochondrial Complex II", The Journal of Biological Chemistry, vol. 286, No. 5, pp. 3717-3728, (2011).
Green et al., "Mitochondria and Apoptosis", Science, vol. 281, No. 5381, pp. 1309-1312, (1998).
Kim et al., "Antiwrinkle effect of adipose-derived stem cell: Activation of dermal fibroblast by secretory factors", Journal of Dermatological Science, vol. 53, pp. 96-102, (2009).
Kim et al., "Functional Regulation of Adipose-Derived Stem Cells by PDGF-D", Stem Cells, vol. 33, pp. 542-556, (2015).
Mao et al., "A Mitochondria-Targeted Vitamin E Derivative Decreases Hepatic Oxidative Stress and Inhibits Fat Deposition in Mice", J. Nutr., vol. 140, pp. 1425-1431, (2010).
Mao et al., "Effect of a mitochondria-targeted vitamin E derivative on mitochondrial alteration and systemic oxidative stress in mice", British Journal of Nutrition, vol. 106, pp. 87-95, (2011).
Matsui, "Synthesis of a-Tocopherol for the Next Century", Journal of Japan Oil Chemists' Society, vol. 45, No. 9, pp. 821-830 and 890, (1996).
Neuzil et al., "Molecular mechanism of 'mitocan'-induced apoptosis in cancer cells epitomizes the multiple roles of reactive oxygen species and Bcl-2 family proteins", FEBS Letters, vol. 580, pp. 5125-5129, (2006).
Neuzil et al., "Vitamin E Analogs, a Novel Group of Mitocans, as Anticancer Agents: The Importance of Being Redox-Silent", Molecular Pharmacology, vol. 71, pp. 1185-1199, (2007).
Placzek et al., "Ultraviolet B-Induced DNA Damage in Human Epidermis Is Modified by the Antioxidants Ascorbic Acid and D-α-Tocopherol", J Invest Dermatol, vol. 124, pp. 304-307, (2005).
Shibata et al., "Suppression of γ-Tocotrienol on UVB Induced Inflammation in HaCaT Keratinocytes and HR-1 Hairless Mice via Inflammatory Mediators Multiple Signaling", J. Agric. Food Chem., vol. 58, pp. 7013-7020, (2010).
Smith et al., "Selective targeting of an antioxidant to mitochondria", Eur. J. Biochem., vol. 263, pp. 709-716, (1999).
Truksa et al., "Mitochondrially Targeted Vitamin E Succinate Modulates Expression of Mitochondrial DNA Transcripts and Mitochondrial Biogenesis", Antioxidants & Redox Signaling, vol. 22, No. 1, pp. 883-900, (2015).

*Primary Examiner* — Nannette Holloman
(74) *Attorney, Agent, or Firm* — Vorys, Sater, Seymour and Pease LLP; Mih Suhn Koh

(57) ABSTRACT

Provided are a cosmetic composition for preventing or ameliorating a ultraviolet-induced skin damage including mitochondria-targeted vitamin E as an active ingredient, as well as a method for protecting skin from ultraviolet-induced skin damage or for ameliorating an ultraviolet-induced skin damage using the same compound.

4 Claims, 7 Drawing Sheets
Specification includes a Sequence Listing.

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
tagggtctag acatgttcag ctttgt             26

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gtgattggtg ggatgtcttc gt                 22

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agatgtggag tgcctgatgt                    20

<210> SEQ ID NO 4
<211> LENGTH: 20
<212> TYPE: DNA

```
<213> ORGANISM: Artificial Sequence
<220> FEATURE:
<223> OTHER INFORMATION: Primer

<400> SEQUENCE: 4
agctagggta catcaaagcc                                              20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cgagatccct ccaaaatcaa                                              20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tgtggtcatg agtcctccca                                              20
```

COSMETIC COMPOSITION FOR PREVENTING OR AMELIORATING SKIN DAMAGE CAUSED BY ULTRAVIOLET LIGHT

SEQUENCE LISTING

The Sequence Listing submitted in text format (.txt) filed on Feb. 23, 2018, named "SequenceListing.txt", created on Feb. 6, 2018 (1.35 KB), is incorporated herein by reference.

TECHNICAL FIELD

The present invention relates to a cosmetic composition for preventing or ameliorating a ultraviolet-induced skin damage. More specifically, the present invention relates to a cosmetic composition for preventing or ameliorating a ultraviolet-induced skin damage, comprising mitochondria-targeted vitamin E (MVE) as an active ingredient.

BACKGROUND ART

Mitochondria are organelles important for both life and death. Mitochondria are major sources of cellular energy and are involved in processes resulting in apoptosis induction. The exact mechanism of apoptosis induction in mitochondria is not clarified in detail, but 'mitocans' are drugs known to induce cancer cell death by targeting mitochondria (Neuzil J et al., *Molecular pharmacology* (2007) 71: 1185-1199; Neuzil J et al., *FEBS letters* (2006) 580: 5125-5129). Mitocans destabilize mitochondria, thereby causing cytosolic release of apoptosis modulators (Green D R et al, (1998) *Science* 281:1309-1312). The indirect pro-oxidant activity of these agents is essential for their actions as anticancer agents (Dong L F et al., (2011) *The Journal of biological chemistry* 286: 3717-3728; Neuzil J et al., *Molecular pharmacology* (2007) 71: 1185-1199).

Meanwhile, mitochondria-targeted vitamin E (MVE) is the compound designed to accumulate within mitochondria. MVE is distributed within the heart, brain, liver, and muscle when administered; and affects mitochondrial dysfunction therein. MVE decreases mitochondrial oxidative damage, thereby inhibiting a range of human disorders, including neurodegenerative diseases, ischemia-reperfusion injury, and aging-associated dysfunctions. Mao et al reported that MVE decreases systemic oxidative stress parameters such as plasma SOD activity, attenuates hepatic oxidative stress and inhibits fat deposition (Mao G et al., (2011) *The British journal of nutrition* 106: 87-95; Mao G et al., *The Journal of nutrition* 140: 1425-1431). However, it has been reported that MVE increased ROS generation in cancer cells and acts as a prooxidant to suppress the proliferation of cancer cells (Dong L F et al., (2011) The Journal of biological chemistry 286: 3717-3728; Neuzil J et al., (2007) Molecular pharmacology 71: 1185-1199). For example, MVE modulates the expression of mitochondrial DNA transcripts and mitochondrial biogenesis. These changes subsequently result in arrest of cell proliferation (Truksa J et al., (2015) *Antioxidants & redox signaling* 22: 883-900). Therefore, MVE has controversial effects, i.e., antioxidant vs. prooxidant according to tissues and/or cells. For example, MVE exhibited protective effects in hepatic cells, but harmful effects in cancer cells. However, the functions of MVE in skin cells have not been identified.

DISCLOSURE

Technical Problem

The present inventors carried out various researches to evaluate the effects of MVE on skin cells. Surprisingly, the present inventors have found that the treatments of human dermal fibroblasts (HDF) and immortalized human keratinocyte cell line (HaCaT) with a low concentration of MVE exhibits a protective effect against ultraviolet (especially UVB), while the treatments with a high concentration of MVE decrease the cell survival rate; and thus that MVE shows dual actions. That is, the present inventors have found that MVE at a low concentration, e.g., of 1 μM or less can be usefully applied to prevent and/or treat ultraviolet-induced skin damages.

Therefore, it is an object of the present invention to provide a cosmetic composition for preventing or ameliorating a ultraviolet-induced skin damage, comprising MVE, i.e., the compound of Formula 1, as an active ingredient.

Technical Solution

In accordance with an aspect of the present invention, there is provided a cosmetic composition for preventing or ameliorating a ultraviolet-induced skin damage, comprising a compound of Formula 1 as an active ingredient:

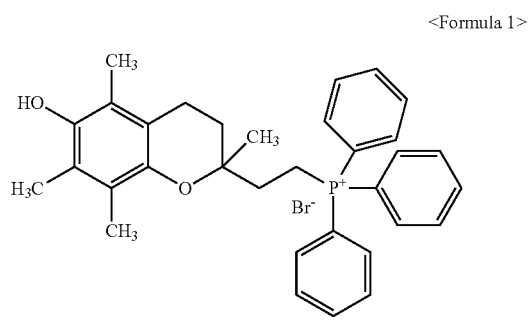 [SMILES: Cc1c(C)c2c(c(C)c1O)CCC(C)(CC[P+](c1ccccc1)(c1ccccc1)c1ccccc1)O2 ; [Br-]]

<Formula 1>

In the cosmetic composition of the present invention, the ultraviolet-induced skin damage may be burns, erythema, or pigmentation, which is generated in the epidermis or dermis by ultraviolet. The amounts of the compound of Formula 1 in the composition may range from 0.1 to 100 μM, preferably 0.5 to 10 μM, based on the total weight of the composition.

Advantageous Effects

It has been found by the present invention that the treatments of human dermal fibroblasts (HDF) and immortalized human keratinocyte cell line (HaCaT) with a low concentration of MVE exhibits a protective effect against ultraviolet (especially UVB), while the treatments with a high concentration of MVE decrease the cell survival rate; and thus that MVE shows dual actions. Therefore, MVE at a low concentration, e.g., of 1 μM or less, can be usefully applied to prevent and/or treat ultraviolet-induced skin damages.

DESCRIPTION OF DRAWINGS

FIG. 1A shows that vitamin E (VE) slightly increased dermal fibroblast survival with UVB irradiation (200 mJ), while MVE decreased dermal fibroblast survival at 10~100 μM concentration. FIG. 1B shows that MVE increased fibroblast proliferation at 100~1000 nM concentration. FIG. 1C shows that MVE protected dermal fibroblasts from UVB at 10~1000 nM concentration. **p<0.01

FIG. 2A shows that MVE significantly increased mRNA expression of collagen and down-regulated that of matrix metalloproteinase 1 (MMP1) in dermal fibroblasts. FIG. 2B shows that mRNA levels of collagen were reduced by UVB but attenuated by MVE treatment and that mRNA levels of MMP1 were induced by UVB but reduced by MVE treatment. FIG. 2C shows that MVE altered protein levels of collagen and MMP1 in fibroblasts.

FIG. 3 shows that MVE reduced production of reactive oxygen species (ROS).

FIG. 4A shows that MVE significantly increased HaCaT cell proliferation in a dose-dependent manner. FIG. 4B shows that MVE increased UVB-reduced cell viability. FIG. 4C shows that UVB increased p53 protein levels in HaCaT cells, while MVE attenuated UVB-induced p53 levels in HaCaT cells. *p<0.05, **p<0.01

FIG. 5 shows that MVE reduced production of ROS.

BEST MODE

Figure 1:
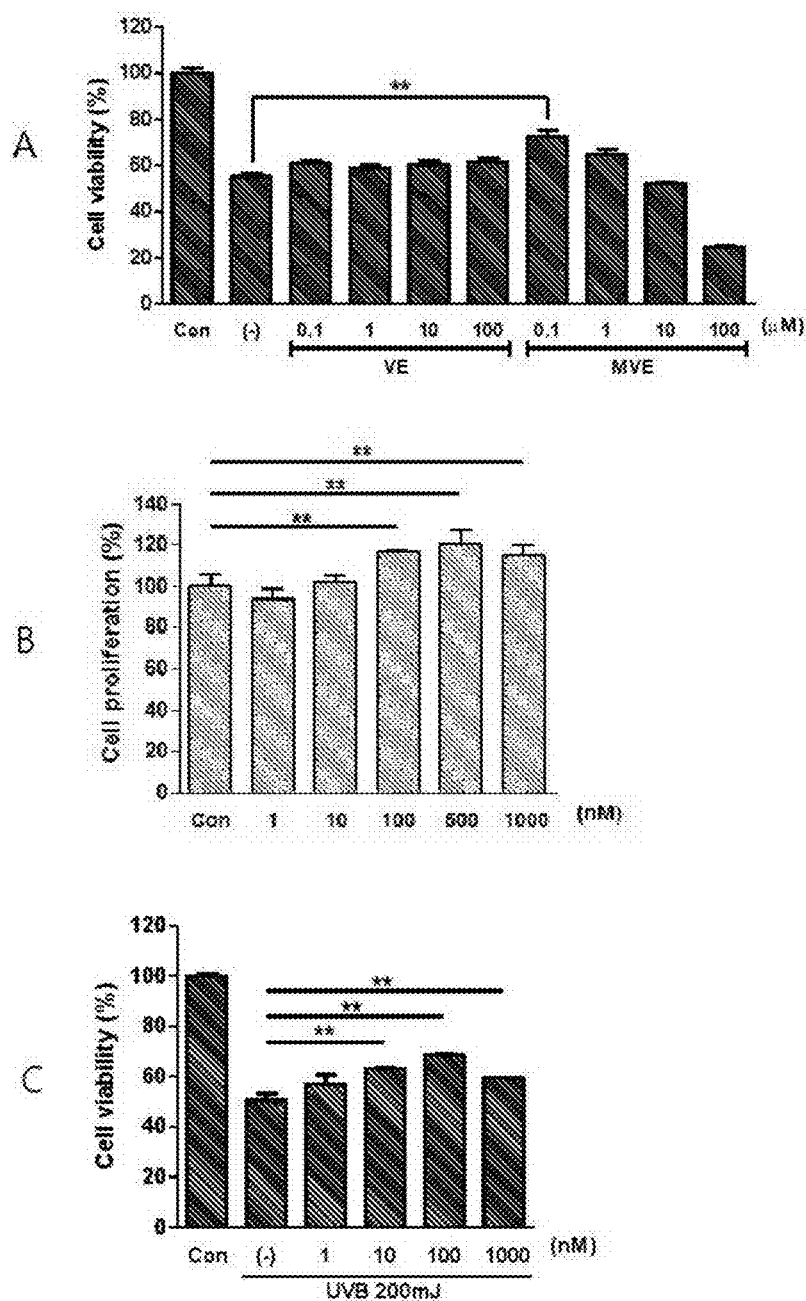
FIG. 1 shows that the compound of Formula 1 (MVE) protected dermal fibroblasts from UVB.

As used herein, the expression "ultraviolet-induced skin damage" refers to the damages caused by interactions between skin cells and ultraviolet coming into contact with the skin. Said interactions include DNA damages caused by ultraviolet, increase of reactive oxygen species, and variations or apoptosis of cells induced therefrom. The symptoms of ultraviolet-induced skin damage include burns, erythema, pigmentation, etc., which are generated in the epidermis or dermis by ultraviolet.

And also, the term "preventing" used herein refers to blocking, delaying, or to delaying skin damages by protecting the skin from ultraviolet-induced skin damages. Accordingly, the expressions "preventing a ultraviolet-induced skin damage" and "protecting a ultraviolet-induced skin damage" have the same meaning.

And also, the term "ameliorating" used herein refers to healing ultraviolet-induced skin damages; inhibiting the progress and/or deterioration of symptoms to stop progressing damages, although complete healing is not provided; or inducing some or all of the symptoms to the direction of healing.

The present invention provides a cosmetic composition for preventing or ameliorating a ultraviolet-induced skin damage, comprising a compound of Formula 1 as an active ingredient:

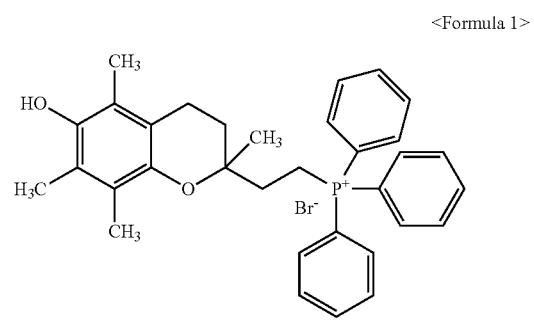 [SMILES: Cc1c(C)c2c(c(C)c1O)CCC(C)(CC[P+](c1ccccc1)(c1ccccc1)c1ccccc1)O2 ; [Br-]]

<Formula 1>

The compound of Formula 1 is a known material and may be prepared according to known methods. For example, the compound of Formula 1 may be prepared according to the methods described in prior arts, such as Mao G et al., (2011) The British journal of nutrition 106: 87-95, Mao G et al., The Journal of nutrition 140: 1425-1431, Makoto Matsui, Journal of Japan Oil Chemists' Society, Vol. 45, no. 9, p 821-890 (1996), Robin A. J. Smith et al., Eur. J. Biochem. 263, 709-716 (1999), and the like.

The cosmetic composition of the present invention may be in various forms and the forms are not limited. That is, the cosmetic composition of the present invention may be in conventional cosmetic composition forms such as cream, pack, lotion, essence, cleansing water, foundation, makeup base, and the like. The cosmetic composition may be formulated, along with a carrier conventionally used in the field of cosmetic composition, according to conventional methods.

It has been found by the present invention that the treatments of human dermal fibroblasts (HDF) and immortalized human keratinocyte cell line (HaCaT) with a low concentration of the compound of Formula 1 (e.g., 1 μM or less) exhibits a protective effect against ultraviolet (especially UVB), while the treatments with a high concentration thereof decrease the cell survival rate; and thus that the compound of Formula 1 shows dual actions. Therefore, the amounts of the compound of Formula 1 in the unit is cosmetic composition may range from 0.1 to 100 μM, preferably 0.5 to 10 μM, based on the total weight of the composition. Of course, the amount may vary depending on the severities of ultraviolet-induced skin damage.

The present invention will be described in further detail with reference to the following examples. These examples are for illustrative purposes only and are not intended to limit the scope of the present invention.

In the following examples, MVE (the compound of Formula 1) was synthesized as described previously (Mao G et al., (2011) The British journal of nutrition 106: 87-95; Mao G et al., The Journal of nutrition 140: 1425-1431). Briefly, trimethylhydroquinone was reacted with myrcene in the presence of (+)-10-camphorsulfonic acid to provide chroman-6-ol, which was protected as the acetate. Oxidative cleavage of the olefin (cat. $OsO_4$, NMO followed by $NaIO_4$), reduction ($NaBH_4$), and deprotection ($K_2CO_3$, MeOH) led to the alcohol, which was converted to an iodide. Treatment of the iodide with triphenylphosphine furnished MVE (the compound of Formula 1).

1. Methods (1) Cell Culture

Human dermal fibroblasts (HDFs) and immortalized keratinocyte cell line (HaCaT) were cultured using DMEM (low, high glucose, Hyclone, Thermo Scientific, Logan, Utah, USA) supplemented with 10% FBS (Gibco, Invitrogen, Carlsbad, Calif., USA), 1% penicillin, and streptomycin (Gibco) at 37° C. with 5% $CO_2$ in a humidified atmosphere (Kim W S et al., (2009) *Journal of dermatological science* 53: 96-102). Said cultures were performed by exchanging with fresh media every two days.

(2) Proliferation Assay and Viability Analysis

HDFs ($3\times10^4$ cells/well) and HaCaT ($4\times10^4$ cells/well) were seeded in 6-well plates. Cells were treated with various concentrations of MVE. Cells were then incubated for 48 hours and the MTT assay was performed. MTT solution (5 mg/ml in phosphate buffered saline) was added to each well at $\frac{1}{20}$ of the media volume, incubated for 2 hours, and then supernatant was removed. Dimethyl sulfoxide (DMSO) was then added to dissolve formazan crystals, and the absorbance was measured at 595 nm using an ELISA reader (TECAN, Grodig, Austria).

(3) Cellular and Mitochondrial ROS Generation Assay

Cellular ROS generation was measured using 2',7'-dichlorodihydrofluorescein diacetate (DCF-DA, Molecular Probes, Eugene, Oreg., USA), as described previously (Hye Kim J et al., *Stem cells* 33: 542-556). Similarly, mitochondrial ROS (mtROS) generation was measured using Mito-Sox (Molecular Probes). Cells were seeded in 6-well plates in 0.2% FBS and cultured overnight. MVE (100 nM) was added with or without DCF-DA (20 μM) or Mito-Sox (5 μM). Each well was imaged every 10 minutes for 40 minutes under standard incubation conditions using an IncuCyte™ ZOOM microscope placed inside an incubator. Image-based analysis of fluorescence intensity was carried out using IncuCyte™ software (Essen Bioscience, MI, USA).

(4) Western Blot Analysis

Cells ($2\times10^5$ cells/ml) were seeded in a 60 mm dish and cultured to 80% confluence. Cells were treated with MVE. Cells were then lysed with 1×RIPA buffer (50 mM Tris-HCl, 0.15 M NaCl, 1 mM EDTA, 1% Triton-X100, pH 7.4, 1% SDS, 50 mM NaF, 1 mM $Na_3VO_4$, 5 mM Dithiothreitol, 1 mg/ml Leupeptin, and 1 mM phenylmethylsulfonyl fluoride). Sample protein (40 μg) was separated in 10-12% SDS-polyacrylamide gels by electrophoresis. Proteins were transferred to PVDF membranes and incubated with antibodies to collagen (1:1000 rabbit source, Santa Cruz Biotechnology, Santa Cruz, Calif., USA) and matrix metalloproteinase 1 (MMP1, 1:1000 rabbit source, Santa Cruz Biotechnology). Membranes were then washed and incubated with horseradish peroxidase-conjugated anti-rabbit IgG antibody (Santa Cruz Biotechnology). Blots were reacted with western reagent (ECL; Millipore Billerica, Ann Arbor, Mass., USA) and exposed to X-ray film.

(5) Reverse Transcription-Polymerase Chain Reaction (RT-PCR)

Total RNA of HDFs and HaCaT was extracted with Trizol reagent followed by reverse transcription to cDNA. The following oligonucleotides were used as primers: collagen type I [5'-TAGGGTCTAGACATGTTCAGCTTTGT-3' (SEQ ID NO: 1) and 5'-GTGATTGGTGGGATGTCT-TCGT-3' (SEQ ID NO: 2)], MMP-1 [5'-AGATGTGGAGT-GCCTGATGT-3' (SEQ ID NO: 3) and 5'-AGCTAGGGTA-CATCAAAGCC-3' (SEQ ID NO: 4)], and control GAPDH [5'-CGAGATCCCTCCAAAATCAA-3' (SEQ ID NO: 5) and 5'-TGTGGTCATGAGTCCTCCCA-3' (SEQ ID NO: 6)]. PCR was carried out in a total volume of 30 μl for PCR amplification of cDNA that was reverse-transcribed from the total RNA. After initial denaturation at 95° C. for 5 minutes, amplification was performed in 35 cycles for 30 seconds at 95° C., 20 seconds at 54° C., and 30 seconds at 72° C. This was followed by a final extension at 72° C. for another 10 minutes. GAPDH mRNA level was used for sample standardization.

(6) Statistical Analysis

Statistical significance was determined using a Wilcoxon signed-rank test or a Student's t-test. $P<0.05$ was considered statistically significant. Statistical analysis was performed using SPSS 18.0 (SPSS, IBM Corp, Armonk, N.Y., USA).

2. Results (1) MVE Protected Dermal Fibroblasts from UVB

When dermal fibroblasts were treated with Vitamin E and MVE having benzopyran in the range from 0.1 to 100 μM, vitamin E slightly increased survival of dermal fibroblasts from UVB irradiation (200 mJ) at 0.1 to 100 μM. However, MVE decreased fibroblast survival in a concentration-dependent manner at the 10 to 100 μM concentrations, while MVE increased fibroblast survival in a concentration-dependent manner at the 0.1 and 1 μM concentrations (FIG. 1A). These results shows that MVE at high concentrations functions as a cytotoxic agent inhibiting cell survival in response to UVB irradiation, while MVE at low concentrations functions as a cytoprotective agent protecting cells from UVB irradiation. Based on these results, the protective effect of MVE was also studied in nM concentration ranges. As the results thereof, MVE increased fibroblast proliferation in the 100~1000 nM range (FIG. 1B, $p<0.01$). In addition, MVE protected fibroblasts from UVB in the 10~1000 nM range (FIG. 10, $p<0.01$). These results indicate that MVE protects fibroblasts from UVB and is more effective that vitamin E.

(2) MVE Altered Expression of Extracellular Matrix Proteins

Figure 2:
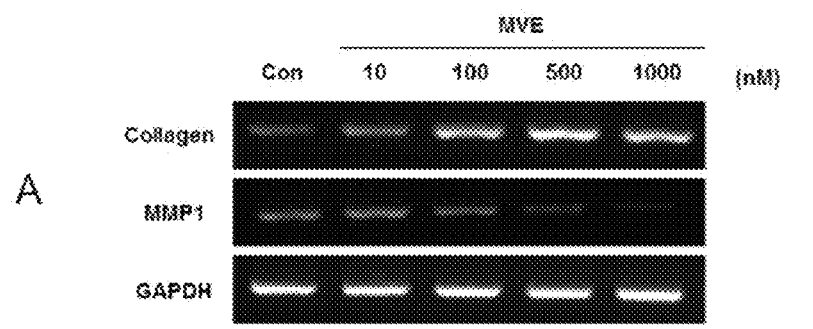
FIG. 2 shows that MVE altered expression of extracellular matrix proteins.
Figure 2:
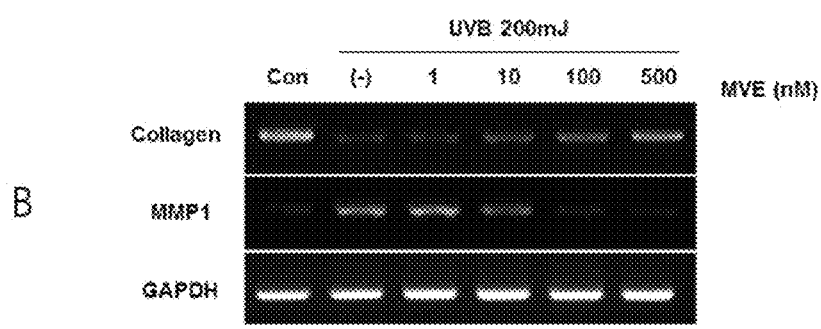
Figure 2:
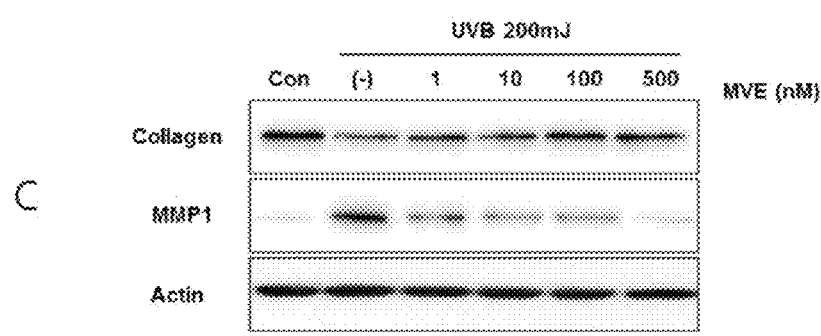

The present inventors examined whether MVE altered the mRNA or protein levels of extracellular matrix (ECM) proteins, such as collagen type I and matrix metalloproteinase 1 (MMP1), in fibroblasts. MVE increased collagen mRNA expression and down-regulated that of MMP1 in dermal fibroblasts (FIG. 2A). The mRNA level of collagen was reduced by UVB irradiation, but attenuated by MVE treatment (FIG. 2B). The mRNA level of MMP1 was increased by UVB, but reduced by MVE treatment (FIG. 2B). In addition, MVE altered the protein levels of collagen and MMP1 in fibroblasts (FIG. 2C).

(3) MVE Reduced Production of Reactive Oxygen Species

Figure 3A:
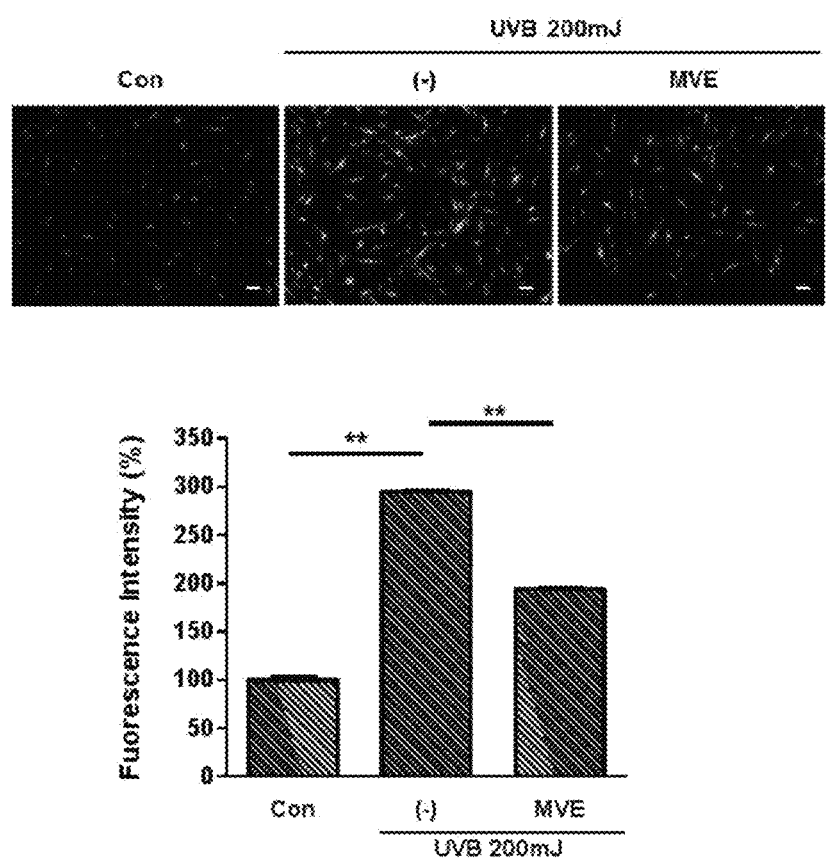
FIG. 3a shows the cytosolic ROS levels measured by using DCF-CA (green). UVB increased the fluorescent signal intensity of DCF-DA in fibroblasts, while MVE (1000 nM) attenuated the signal intensity of DCF-DA.
Figure 3B:
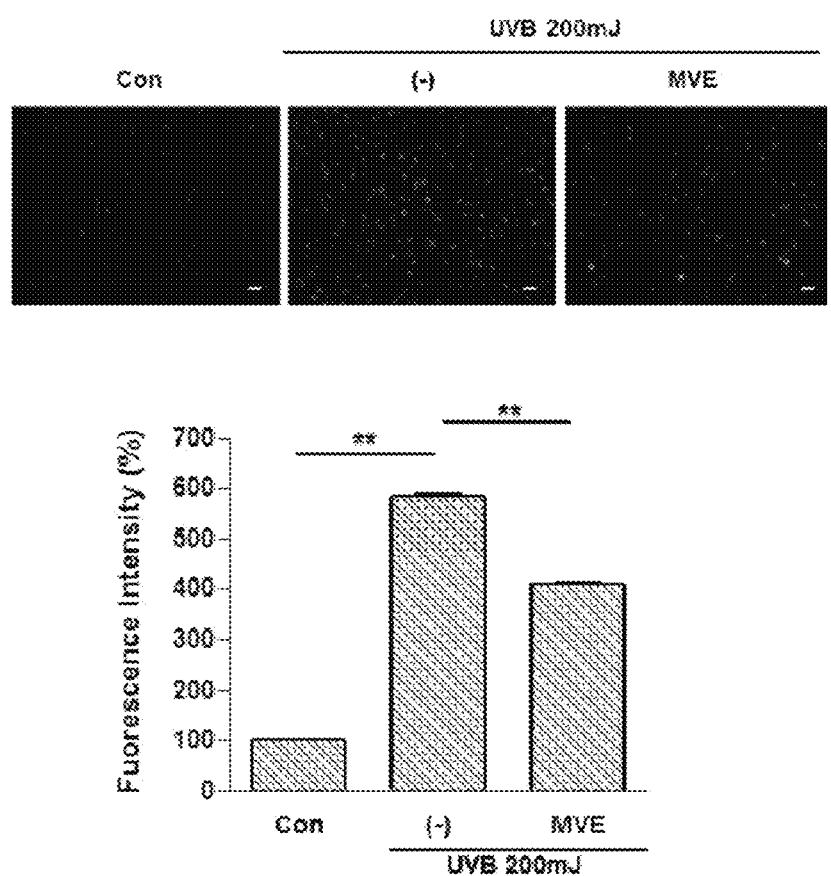
FIG. 3b shows the mitochondria ROS production measured by using mito-Sox (red). Likewise, UVB increased the fluorescent signal intensity of mito-Sox in fibroblasts, while MVE (1000 nM) reduced the signal intensity of mito-Sox. Scale bar=100 μm, **p<0.01

Because UVB reportedly generates reactive oxygen species (ROS) and induced apoptosis in skin, ROS levels were measured after MVE treatment. First, the cytosolic ROS level was measured using DCF-CA (green, FIG. 3a). UVB increased the fluorescent signal intensity of DCF-DA in fibroblasts, while MVE (1000 nM) attenuated the signal intensity of DCF-DA ($p<0.01$). Mitochondria ROS production was measured using mito-Sox (red, FIG. 3b). UVB increased the fluorescent signal intensity of mito-Sox in fibroblasts, while MVE (1000 nM) reduced the signal intensity of mito-Sox ($p<0.01$). These results indicate that MVE protects dermal fibroblasts from UVB via reducing ROS generation.

(4) MVE Protected HaCaT Cells from UVB

Figure 4:
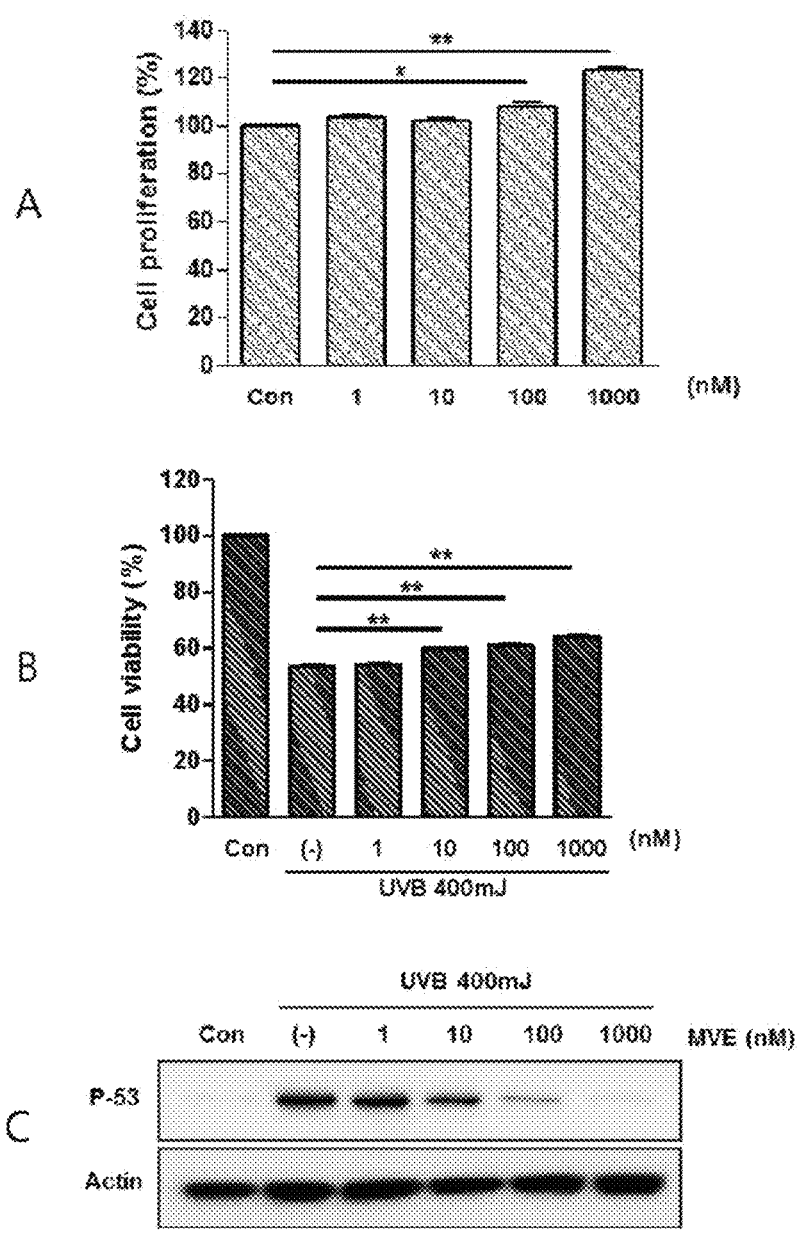
FIG. 4 shows that MVE protected HaCaT cells from UVB.

The protective effects of MVE in epidermal skin cells were also investigated using the HaCaT cell line. MVE significantly increased proliferation of HaCaT cells in a dose-dependent manner (FIG. 4A, $p<0.05$). In addition, MVE increased the UVB-reduced cell viability (FIG. 4B, $p<0.01$). UVB induced p53 protein levels in HaCaT cells, while MVE reduced p53 levels in HaCaT cells (FIG. 4C).

(5) MVE Reduced Production of Reactive Oxygen Species

Figure 5A:
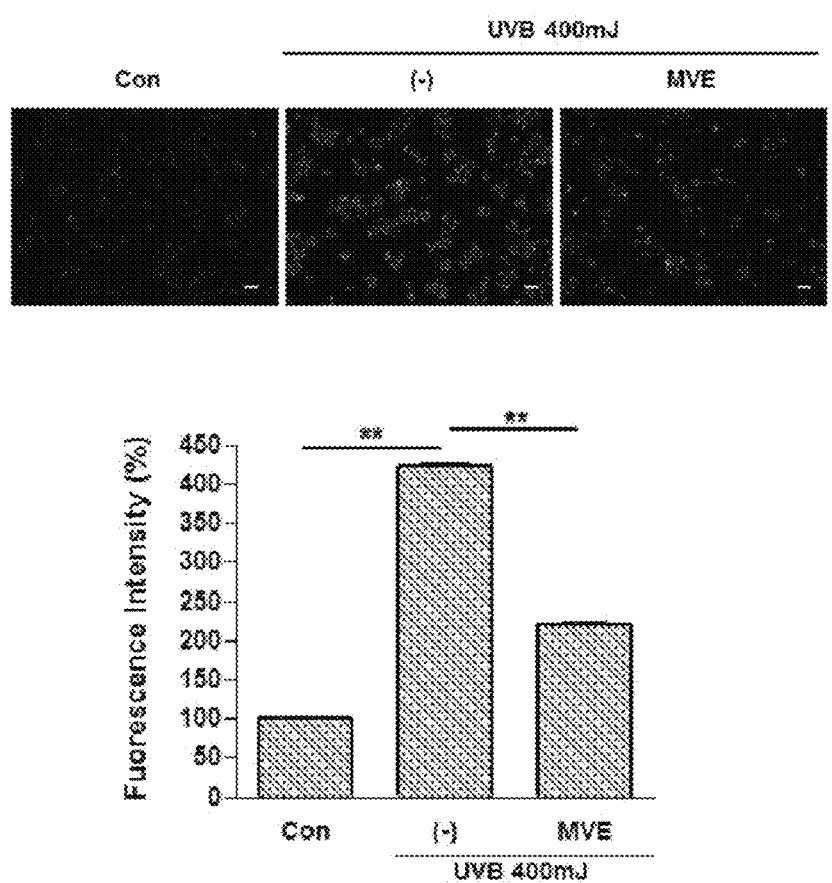
FIG. 5a shows the cytosolic ROS level measured by using DCF-CA (green). UVB increased the fluorescent signal intensity of DCF-DA in HaCaT cells, while MVE (1000 nM) attenuated the signal intensity of DCF-DA.
Figure 5B:
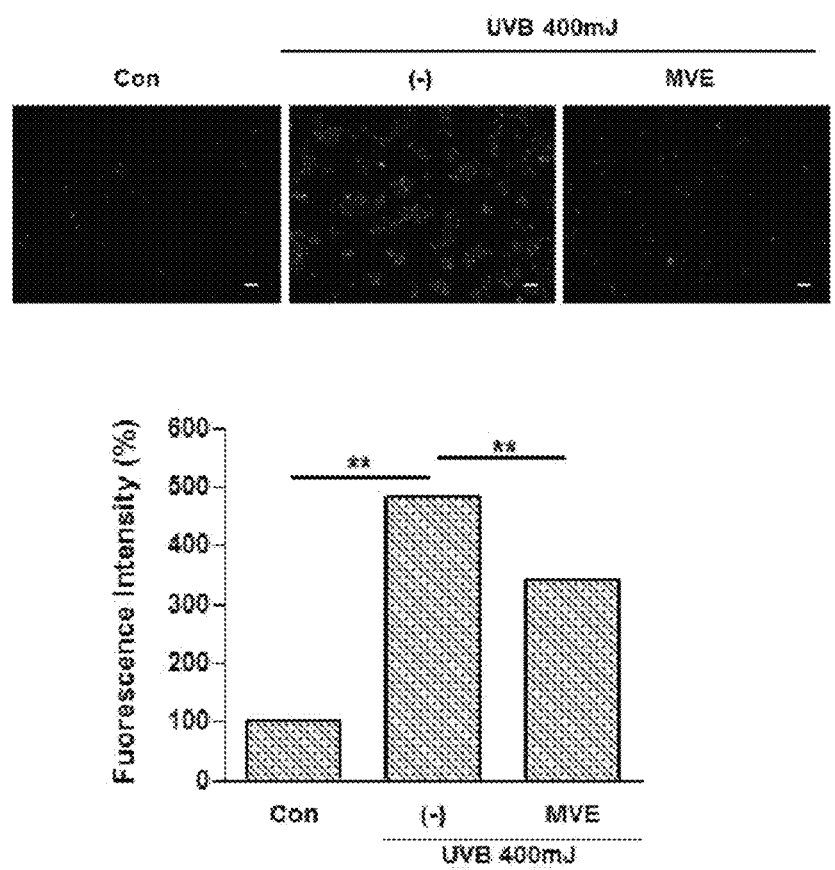
FIG. 5b shows the mitochondria ROS production measured by using mito-Sox (red). UVB increased the fluorescent signal intensity of mito-Sox in HaCaT cells, while MVE (1000 nM) reduced the signal intensity of mito-Sox. Scale bar=100 μm, **p<0.01

ROS levels were also measured after MVE treatment in HaCaT calls. The cytosolic ROS level was measured using DCF-CA. UVB increased the fluorescent signal intensity of DCF-DA in HaCaT cells, while MVE (1000 nM) attenuated the signal intensity of DCF-DA (FIG. 5a, p<0.01). Mitochondrial ROS production was also measured using mito-Sox. UVB increased the fluorescent signal intensity of mito-Sox in HaCaT cells, while MVE (1000 nM) reduced the signal intensity of mito-Sox (FIG. 5b, p<0.01). These results indicate that MVE protects dermal fibroblasts from UVB via reducing ROS generation.

3. Discussion

The present study investigated the protective effects of MVE against UVB in dermal fibroblasts and epidermal HaCaT cells. MVE increased the proliferation and survival of fibroblasts at low concentration (i.e., nM ranges). In addition, MVE increased collagen production and downregulated MMP1 expression. MVE also increased the proliferation and survival of HaCaT cells. UVB increased ROS production in fibroblasts and HaCaT cells, while MVE decreased ROS production in these cells. These results collectively suggest that low dose MVE protects skin from UVB irradiation. Therefore, MVE can be used as a cosmetic raw material for blocking ultraviolet.

Vitamin E is a group of compounds that include both tocopherols and tocotrienols. As a fat-soluble antioxidant, vitamin E inhibits the production of ROS when fat undergoes oxidation. Vitamin E acts as a peroxyl radical scavenger, preventing the propagation of free radicals in tissues. It is known that vitamin E protects dermal fibroblasts and epidermal keratinocytes from UVB. For example, γ-tocotrienol protected HaCaT keratinocytes from UVB induced inflammation (Shibata A et al., (2010) *Journal of agricultural and food chemistry* 58: 7013-7020). And also, D-alpha-tocopherol prevented UVB-induced DNA damage in human epidermis (Placzek M et al., (2005) *The Journal of investigative dermatology* 124: 304-307). Vitamin E is included as antioxidants in many sunscreens and lotions.

In the present study, MVE showed a dual mode of actions. That is, at low concentrations (<1 μM), MVE protected dermal fibroblasts and epidermal HaCaT cells from UVB via scavenging ROS production (FIG. 1A). However, MVE inhibited the survival of dermal fibroblasts at high concentrations (>1 μM). Although the mechanism of action is not yet clarified, MVE acts as an antioxidant at low concentrations and as a prooxidant at high concentrations in normal cells.

In summary, it has been found by the present invention that MVE exhibits remarkably excellent ultraviolet blocking activity, as compared to vitamin E commonly having a benzopyran moiety in its molecule. Low concentration MVE protected dermal fibroblasts and epidermal HaCaT cells from UVB irradiation by scavenging ROS in these cells. MVE also increased collagen production and decreased MMP1 expression. Therefore, MVE can be developed and used for cosmetic raw materials to replace vitamin E.

The invention claimed is:

1. A cosmetic composition for preventing or ameliorating an ultraviolet-induced skin damage, comprising the compound of Formula 1 as an active ingredient in an amount of 0.5 μM to 10 μM based on the total weight of the composition:

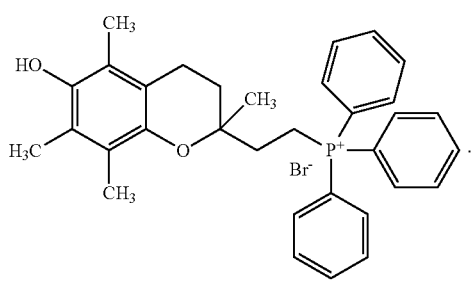

<Formula 1>

2. The cosmetic composition according to claim 1, wherein the ultraviolet-induced skin damage is burns, erythema, or pigmentation, which is generated in the epidermis or dermis by ultraviolet.

3. A method for protecting skin from ultraviolet-induced skin damage or for ameliorating an ultraviolet-induced skin damage comprising applying a cosmetic composition to a subject in need thereof, the cosmetic composition comprising an effective amount of the compound of Formula 1 in an amount of 0.5 μM to 10 μM based on the total weight of the composition:

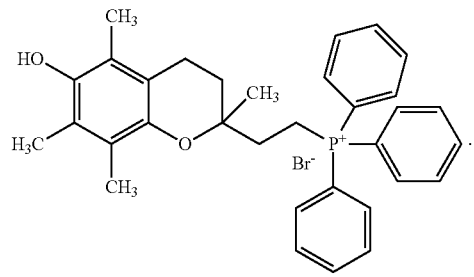

<Formula 1>

4. The method according to claim 3, wherein the ultraviolet-induced skin damage is burns, erythema, or pigmentation, which is generated in the epidermis or dermis by ultraviolet.

* * * * *